(12) United States Patent
Loumaye

(10) Patent No.: US 7,671,027 B2
(45) Date of Patent: Mar. 2, 2010

(54) USE OF GNRH AGONISTS TO SUPPORT THE LUTEAL PHASE DURING INFERTILITY TREATMENT

(75) Inventor: Ernest Loumaye, Massongy (FR)

(73) Assignee: PregLem S.A., Geneva (CH)

( * ) Notice: Subject to any disclaimer, the term of this patent is extended or adjusted under 35 U.S.C. 154(b) by 747 days.

(21) Appl. No.: 10/540,228

(22) PCT Filed: Dec. 29, 2003

(86) PCT No.: PCT/IB03/06205

§ 371 (c)(1),
(2), (4) Date: Jun. 21, 2005

(87) PCT Pub. No.: WO2004/058269

PCT Pub. Date: Jul. 15, 2004

(65) Prior Publication Data

US 2006/0069031 A1   Mar. 30, 2006

Related U.S. Application Data

(60) Provisional application No. 60/448,468, filed on Feb. 21, 2003.

(30) Foreign Application Priority Data

Dec. 27, 2002  (FR) .................................. 02 16810

(51) Int. Cl.
*A61K 38/00* (2006.01)
*A61K 38/24* (2006.01)
*A61K 35/48* (2006.01)
*C07K 16/00* (2006.01)

(52) U.S. Cl. ................ 514/15; 514/12; 530/313; 530/328; 530/398; 530/399; 424/559; 424/561; 424/562

(58) Field of Classification Search .............. 514/15, 514/12; 530/313, 328, 398, 399; 424/559, 424/561, 562

See application file for complete search history.

(56) References Cited

U.S. PATENT DOCUMENTS 5,538,948 A * 7/1996 Jacobs ................. 514/12
6,489,288 B1 * 12/2002 Lunenfeld .............. 512/15

FOREIGN PATENT DOCUMENTS

WO    WO 95/16459    6/1995

OTHER PUBLICATIONS

Lemay, Andre et al. "Sensitivity of pituitary and corpus luteum responses to single intranasal administration of (D-Ser[TBU]$^6$-des-Gly-NH$_2$$^{10}$) luteinizing hormone-releasing hormone ethylamide (Buserelin) in normal women" *Fertility and Sterility*, 37(2):193-200 (1982).
Molloy, Brian et al. "Ovulation induction in clomiphene nonresponsive patients: the place of pulsatile gonadotropin-releasing hormone in clinical practice" *Fertility and Sterility*, 43(1):26-33 (1985).
Lemay, Andre et al. "Gonadotroph and corpus luteum responses to two successive intranasal doses of a luteinizing hormone-releasing hormone agonist at different days after the midcycle luteinizing hormone surge" *Fertility and Sterility*, 39(5):661-667 (1983).
Schmidt-Sarosi, Cecilia et al. "Ovulation triggering in clomiphene citrate-stiumlated cycles: human chorionic gonadotropin versus a gonadotropin releasing hormone agonist" *Journal of Assisted Reproduction and Genetics*, 12(3):167-174 (1985).
Hanker, J.P. et al. "Frequency-varied versus unvaried pulsatile LH-RH substitution in hypothalamic amenorrhea" *Europ. J. Obstet. Gynec. reprod. Biol.*, 17:103-119 (1984).
Volpe, A. et al. "Pregnancy following combined growth hormone-pulsatile GnRH treatment in a patient with hypothalamic amenorrhoea" *Human Reproduction*, 5(3):345-347 (1990).
Mitwally, Mohamed F. M. et al., "Use of an Aromatase Inhibitor for Induction of Ovulation in Patients With an Inadequate Response to Clomiphene Citrate," *Obstetrical & Gynecological Survey*, vol. 56(7):421-422 (2001).
Tsafriri, S. et al., "Oocyte Maturation Involves Compartmentalization and Opposing Changes of cAMP Levels in Follicular Somatic and Germ Cells: Studies Using Selective Phosphodiesterase Inhibitors," *Developmental Biology*, vol. 178:393-402 (1996).

* cited by examiner

*Primary Examiner*—Jon P Weber
*Assistant Examiner*—Abdel A Mohamed
(74) *Attorney, Agent, or Firm*—Lahive & Cockfield, LLP; Debra J. Milasincic, Esq.

(57) ABSTRACT

The present invention concerns the use of an agonist of an hypothalamic hormone for the preparation of a pharmaceutical agent to support the luteal phase during infertility treatment of female mammals and more specifically of woman. According to this invention, the pharmaceutical agent is suitable to be used for supporting the luteal phase after a spontaneous ovulation or after stimulation of follicular growth, trigger of final follicular maturation and ovulation with one or several additional agents.

30 Claims, No Drawings

SEQUENCE LISTING

<160> NUMBER OF SEQ ID NOS: 6

<210> SEQ ID NO 1
<211> LENGTH: 10
<212> TYPE: PRT
<213> ORGANISM: Homo sapiens

<400> SEQUENCE: 1

Glu His Trp Ser Tyr His Leu Arg Pro Gly
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: t-butylserine

<400> SEQUENCE: 2

Glu His Trp Ser Tyr Ser Leu Arg Pro
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu His Trp Ser Tyr Leu Leu Arg Pro
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu His Trp Ser Tyr Trp Leu Arg Pro Gly
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: t-butylserine
<220> FEATURE:
<221> NAME/KEY: MOD_RES
<222> LOCATION: (10)..(10)
<223> OTHER INFORMATION: aza-glycine

<400> SEQUENCE: 5

Glu His Trp Ser Tyr Xaa Leu Arg Pro Xaa
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 2-Naphthylalanine

```
<400> SEQUENCE: 6

Glu His Trp Ser Tyr Xaa Leu Arg Pro Gly
1               5                   10
```

USE OF GNRH AGONISTS TO SUPPORT THE LUTEAL PHASE DURING INFERTILITY TREATMENT

RELATED APPLICATIONS

This application is a 35 U.S.C. §371 filing of International Application Number PCT/IB2003/006205 which was filed Dec. 29, 2003, which claims priority to French Patent Application No. 0216810 filed on Dec. 27, 2002. International Application Number PCT/IB2003/006205 also claims priority to U.S. Provisional Application No. 60/448,468, which was filed on Feb. 21, 2003. The contents of the aforementioned applications are hereby incorporated herein by reference.

FIELD OF THE INVENTION

The present invention concerns the use of an agonist of an hypothalamic hormone for the preparation of a pharmaceutical agent to support the luteal phase during the infertility treatment of female mammals and more specifically of women.

BACKGROUND OF THE INVENTION

The menstrual cycle in woman is composed of three distinct phases (Yen S, and Jaffe R. 1986, Reproductive Endocrinology: Physiology, Pathophysiology and Clinical Management, W.B. Saunders Company, Philadelphia, Pa., USA.):

1. The follicular phase during which several ovarian follicles are recruited, followed by the selection and the dominance of one follicle. This phase lasts approximately 12 days and is characterized by a progressive rise of serum estradiol levels and low progesterone levels. This phase is the result of the secretion of a hormone called FSH ("Follicle Stimulating Hormone") by the anterior pituitary gland.

2. A peri-ovulatory phase (also called ovulation) which lasts approximately 48 hours and is characterized by a sudden rise in serum LH ("Luteinizing Hormone", another hormone secreted by the pituitary gland). This phase ends when the "*corpus luteani*" is formed. This phase includes the following sequence of events:

The Final Follicular Maturation:
The follicle steroidogenesis switches from a preferential secretion of estradiol to a preferential secretion of progesterone.
The oocyte resumes its meiosis.
The Ovulation:
The follicle is ruptured and the oocyte leaves the ovary
The Corpus Luteum Formation
The empty follicle is re-organized to form the corpus luteum.

3. The luteal phase during which the corpus luteum secretes large amount of progesterone as well as somewhat smaller quantities of 17 OH-progesterone, estradiol, estrone and relaxin. This phase lasts approximately 14 days and depends of an appropriate secretion of LH by the pituitary gland. During the luteal phase, progesterone works together with estradiol on endometrial cells to provide an environment favorable for the embryo implantation.

The luteal phase can be deficient. This can result from a deficit in progesterone secretion by the corpus luteum. In this case, serum progesterone levels are below 10 ng/ml. The luteal deficiency can also result from a shortening of the luteal phase (i.e. less than 11 days). The clinical consequences of a luteal phase deficiency are failure of embryo implantation, or a miscarriage if the pregnancy has already started (Yen S, and Jaffe R. 1986, Reproductive Endocrinology: Physiology, Pathophysiology and Clinical Management, W.B. Saunders Company, Philadelphia, Pa., USA.).

A luteal phase deficiency is a common characteristic of cycles during which follicular development is stimulated with pharmacological agents for the treatment of infertility. This has been reported both in anovulatory patients undergoing ovulation induction therapy, and in ovulatory patients undergoing stimulation of multiple follicular development prior to intra-uterine insemination (IUI) or prior to Assisted Reproductive Techniques (ART) such as in vitro fertilisation (IVF) and intra-cytoplasmic insemination (ICSI).

The luteal phase deficiency has been observed in cycles stimulated with clomiphene citrate, FSH/hMG, FSH/hMG with a GnRH agonist pre-treatment ("Gonadotrophin releasing hormone") as well as FSH/hMG with a GnRH antagonist co-treatment (Beckers N G et al. 2003, Comparison of non-supplemented luteal phase characteristics following the administration of r-hCG, r-hLH or GnRH agonist to induce final oocyte maturation in in vitro fertilisation patients. J. Clin. Endocrinol. Metab. 88: 4186-4192; Pritts E. A. and Atwood A. K. 2002, Luteal support in infertility treatment: a meta-analysis of the randomized trials. Hum Reprod 17: 2287-2299). The luteal phase deficiency is mainly attributed to the elevated serum estradiol levels resulting from the pharmacological stimulation of the ovaries.

The pharmacological support of the luteal phase, also called "luteal supplementation", is mandatory in infertility treatments in order to significantly increase the embryo implantation rate, the pregnancy rate and to reduce the miscarriage rate (Pritts E. A. and Atwood A. K. 2002, Luteal support in infertility treatment: a meta-analysis of the randomized trials. Hum Reprod 17: 2287-2299).

Two drugs are routinely used for the luteal support. The first is natural progesterone, the second is the human chorionic gonadotropin (hCG). Progesterone is administered intra-muscularly (IM) or vaginally. The therapeutic objective is to increase serum progesterone levels. HCG is administered intra-muscularly (IM) or sub-cutaneously (SC). HCG is a naturally occurring agonist of LH and therefore it stimulates progesterone secretion by the corpus luteum.

In ART treatments, a luteal support by hCG or progesterone IM significantly increases pregnancy rate (Pritts E. A. and Atwood A. K. 2002, Luteal support in infertility treatment: a meta-analysis of the randomized trials. Hum Reprod 17: 2287-2299). The odds to obtain a pregnancy with hCG compared to no luteal support is 2.72 (CI: 1.56-4.90; p<0.05) and with progestérone IM is 2.38 (CI: 1.36-4.27; p<0.05). Progesterone administered by vaginal route, although superior to no luteal support, is not as effective as progesterone IM. With vaginal progesterone the odds to obtain a pregnancy is 2.11 with a C.I. of 0.95-4.67 (NS). Furthermore, the relative efficacy of IM progesterone vs vaginal progesterone is 1.33 with a C.I. of 1.02-1.75, in favor of the IM route (p<0.05) (Pritts E. A. and Atwood A. K. 2002, Luteal support in infertility treatment: a meta-analysis of the randomized trials. Hum Reprod 17: 2287-2299).

The drawbacks of IM progesterone are: (i) the injections must be performed daily for more than two weeks, (ii) the progesterone solution is oily and therefore injections are painful, (iii) these injections can trigger an inflammatory reaction and even a sterile abcess, (iv) IM injections are not easy for self-administration by the patient therefore often requiring paramedical assistance.

The drawbacks of hCG as luteal support are: (i) its use is associated with a rare but potentially life-threatening adverse event called ovarian hyperstimulation syndrome (OHSS), (ii) it must be injected, (iii) it induces a false positive pregnancy test, delaying the pregnancy diagnostics, (iv) it is a biological product extracted from urine or from culture media containing animal sera, and therefore presents a, at least theoritical risk, of contamination by infectious particles (e.g. viruses or prions) (Reichl H et al., 2002 Prion transmission in blood and urines: what are the implications for recombinant and urinary-derived gonadotropins Hum Reprod 17: 2501-2508). For all these reasons many doctors refrain of using hCG as luteal support.

SUMMARY OF THE INVENTION

Therefore, the object of the present invention is to avoid the above-mentioned drawbacks. This has been achieved by the use of an agonist of an hypothalamic hormone, i.e. an agonist of GnRH, for the preparation of a pharmaceutical preparation to support the luteal phase during the infertility treatment of female mammals and more specifically of woman. According to this invention, the pharmaceutical agent is suitable to support the luteal phase after a spontaneous ovulation or after stimulation of follicular growth, triggering final follicular maturation and ovulation with one or more additional agents.

DETAILED DESCRIPTION OF THE INVENTION

In the detailed description of the invention application that follows, the following terms correspond to the following definitions:

The term "Administration" means to give a medication to a patient

The term "Follicle" refers to a structure in the ovary that contains and nurtures the oocyte. The oocyte is the female gamete or the female germinal cell.

In its final phase of development, the follicle becomes antral. This means that it has a cavity filled with fluid. At this stage of development, follicle growth is dependant from the pituitary FSH secretion. Follicle growth can be followed by measuring the cavity diameter with an ultrasound device. Typically, a pre-ovulatory follicle diameter measures between 16 and 24 mm (Balasch J. 2001. Inducing follicular development in anovulatory patients and normally ovulating women: current concepts and the role of recombinant gonadotropins. In Textbook of Assisted Reproductive Techniques eds D. K. Gardner, A. Weissman, C. M. Howles, Z. Shoham. Martin Dunitz 2001 pp 425-446).

"Cumulus-oocyte complex" refers to an oocyte surrounded by a mucinous matrix. The oocyte is freed of the cumulus after ovulation, during fertilisation. This occurs mainly thanks to an enzyme called hyaluronidase which is secreted by spermatozoa.

The term "Peri-Ovulatory phase" includes the events resulting from the sharp increase in serum LH at mid-cycle:

"Final follicular maturation" refers to the biochemical and biological modifications occurring in the follicle and in the oocyte-cumulus complex during the mid-cycle LH rise but before the follicle rupture and the oocyte release. Briefly, these modifications include: (i) a change in granulosa cell steroidogenesis which switches from a mainly estradiol secretion towards a mainly progesterone secretion, (ii) the resumption of the oocyte meiosis which transforms the oocyte from a germinal vesicle stage into a metaphase II stage.

"Ovulation" refers to the process by which the oocyte leaves the ovary. First, the follicle makes protrusion at the surface of the ovary, it then ruptures and the oocyte-cumulus complex is expulsed with the follicular fluid.

"Corpus Luteum Formation" refers to the re-organisation of the empty follicle after the oocyte-cumulus complex expulsion. Granulosa cells and theca cells (the two main cell populations of the follicle) undergo luteinization and neo-vascularisation to become a progesterone-secreting organ.

It is noteworthy that in medical jargon the wording "ovulation" is often used to describe both the peri-ovulatory events and the follicular rupture itself.

The term "Luteal Phase" refers to the lifespan of the corpus luteum during a spontaneous cycle without conception. Its lifespan is on average 14 days. The luteal phase begins the day after the mid-cycle rise in LH and finishes the day before the first day of menstruation.

The term "Luteal Support" defines the therapeutic interventions during the luteal phase aiming at supplementing or substituting the corpus luteal function for improving the embryo implantation and the early pregnancy development. Currently, two therapeutic agents are used for luteal support i.e. hCG and natural progesterone.

The term "Assisted Reproductive Technics" (ART) refers to medical interventions aiming at obtaining a pregnancy. These methods imply, by definition, manipulation of the male gametes (the spermatozoa) and/or the female gamete (the oocyte). In the most often used ART methods, follicular growth is first stimulated with one or several pharmaceutical agents. This is followed by methods for facilitating fertilization such as intra-uterine insemination (IUI) or in vitro fertilization (IVF). IUI consists in introducing a spermatozoa suspension into the uterine cavity using a fine catheter. IVF consists first to retrieve the oocytes from the ovary using a transvaginal echoguided aspiration needle. Then the oocytes are co-incubated with spermatozoas in vitro for obtaining a natural fertilization. ICSI, which is a variation of the IVF method, is identical to IVF except that the fertilization is obtained by micro-injecting one spermatozoa directly in the oocyte cytoplasm. The embryos resulting from IVF and ICSI are maintained in culture medium during a few days before being replaced in the patient's uterus or to be frozen for subsequent replacement.

The term "Gonadotrophin releasing hormone (GnRH)" refers to a peptidic hormone secreted by a specific area of the brain called hypothalamus. This decapeptide plays a pivotal role in the mechanisms of reproduction in many species and specifically in humans. GnRH acts on a specific cell population in the anterior pituitary gland where it bounds to a specific membrane receptor. It activates this receptor provoking an immediate secretion of LH and FSH in the blood stream.

The term "GnRH agonist" refers to synthetic or natural analogs of the native GnRH which have the capacity to recognise and activate GnRH receptors. The GnRH agonist analogs used in the present invention may be selected among a native GnRH from mammals or any other animal species, or a recombinant, or a synthetic peptide agonist of GnRH, or a nonpeptide agonist of GnRH, or a chimeric molecule of GnRH. The latter molecule may include a functional portion, peptidic or non-peptidic, of GnRH and will be obtained by molecular biology methods known by those skilled in the art.

The term "Follicle Stimulating Hormone (FSH)" refers to a pituitary hormone which stimulates ovarian follicle growth. FSH is part of a hormone family called the gonadotropins. Human FSH therapeutic preparations are obtained by extraction from biological fluids rich in FSH such as the urine of postmenopausal women. FSH can also be extracted from culture medium in which genetically modified cells produce human FSH (e.g. DNA recombination of CHO cells; Loumaye E., Howles C. 1999 Superovulation of Assisted Conception The new Gonadotrophins. In Textbook of In Vitro Fertilization and Assisted Reproduction. P. Brinsden Eds, Parthenon Publishing). For the present invention the term FSH refers to a mix of several FSH isoforms, as well as to one specific FSH isoform which can be naturally occurring or obtained by a technical process. The term FSH also refers to hybrid molecules or chimeric molecules, to peptides and peptidomimetics which display FSH activity either by activation of the FSH receptor or by biochemical interaction at the post-receptor level in FSH target cells.

The term FSH also includes therapeutic preparations such as hMG (human menopausal gonadotrophins) or recombinant FSH preparations in which small amount of LH and/or hCG are added.

The term "Selective estrogen receptors modulators (SERM)" refers to all chemical or polypeptide compound which acts totally or partially as activator of the oestrogen receptors, in particular at hypothalamic and pituitary levels. Examples of SERM include clomiphen (e), tamoxifen(e), and raloxifen(e).

The term "Aromatase inhibitor" refers to all chemical, steroidal, and polypeptide compounds which block the activity of an enzyme called aromatase. This enzyme catalyses the conversion of androgens into oestrogens. Examples of aromatase inhibitors include anastrozole, letrozole and exemestane.

The term "Phosphodiesterase Inhibitors" refers to all chemical compounds which block or inhibit phosphodiesterases. Phosphodiesterases are enzymes inactivating cyclic nucleotides such as cyclic AMP and cyclic GMP. Inhibition of this activity results in the accumulation of these cyclic nucleotides prolonging in the target tissue, the signal induced by FSH ou LH. An example of phosphodiesterase inhibitor is theophyline.

GnRH is a neuropeptide which stimulates LH and FSH secretion by the pituitary gland. In humans, its amino-acid composition is <Glu$^1$-His$^2$-Trp$^3$-Ser$^4$-Tyr$^5$-His$^6$-Leu$^7$-Arg$^8$-Pro$^9$-Gly$^{10}$-NH$_2$ (SEQ ID NO: 1). In post-pubertal female, pulsatile release of GnRH by the hypothalamus plays a key role in fertility by inducing the secretion of gonadotropins (FSH and LH) resulting into the menstrual cycle. Conditions associated with GnRH secretion deficiency (WHO group I anovulation: e.g. Kallmann's syndrome and weight-loss related amenorrhea) are therefore characterised by absence of ovulation, absence of spontaneous menstruation (amenorrhea) and infertility. This condition has been successfully treated by administration of synthetic, native GnRH (Shoham Z. et al. 1990; Induction of ovulation with pulsatile GnRH. Baillières Clinb Obstet Gynaecol. 4: 589-608). In order to be effective, GnRH administration has to be pulsatile, at a frequency of one pulse every 60 to 90 minutes at the beginning of the follicular phase and approximately one pulse every 2 to 4 hours during luteal phase (Hanker J. P. et al.; 1984, Frequency-varied versus unvaried pulsatile LH-RH substitution in hypothalamic amenorrhea). In addition, it is administered intravenously or subcutaneously which imposes to patients to carry a portable pump for several weeks. Beside the burden of carrying this pump, adverse events such as phlebitis, sepsis and abcess at the injection site are not rare (Molloy B. G. et al. 1985; Ovulation induction in clomiphene nonresponsive patients: the place of pulsatile gonadotrophin-releasing hormone in clinical practice. Fertil. Steril. 43: 26-33). One study has assessed nasal administration of native GnRH to maintain the luteal phase after inducing follicular development and ovulation by intravenous administration of native GnRH. GnRH was again administered every 4 hours to mimic endogenous GnRH secretory pattern. In half of the patients, this was completely ineffective to support the luteal phase, and efficacy was found to be highly dependent of the follicular phase pulse frequency (Hanker J. P. et al.; 1984, Frequency-varied versus unvaried pulsatile LH-RH substitution in hypothalamic amenorrhea. Europ. J. Obstet. Reprod. Biol. 17: 103-119). Frequently administered native GnRH by intravenous and subcutaneous routes has also been attempt in patients with dysfunctional GnRH secretion, but with very low efficacy and similar adverse outcome (Molloy B. G. et al. 1985; Ovulation induction in clomiphene nonresponsive patients: the place of pulsatile gonadotrophin-releasing hormone in clinical practice. Fertil. Steril. 43: 26-33).

Analogs derived from native GnRH structure have been synthesized and selected for an agonist activity that is enhanced compared to the native peptide. This increased activity is mainly due to an enhanced resistance to degradation and a higher affinity for the pituitary GnRH receptor (Loumaye E et al., 1982, Binding affinity and biological activity of gonadotropin releasing hormone agonists in isolated pituitary cells. Endocrinology; 111:730-736). Although initially designed as potential substitutes to native GnRH for stimulating gonadal functions, these agonists were found to induce the opposite effect by rapidly desensitising pituitary cells. For that reason, in clinics, they are used for reducing LH and FSH secretion and suppress gonadal functions both in man and woman. The main therapeutic indications of these agonists are prostate cancer, endometriosis, and the prevention of premature rise of LH during stimulation of follicular development prior to ART (Loumaye E. 1990 The control of endogenous secretion of LH by gonadotrophin-releasing hormone agonists during ovarian hyperstimulation for in-vitro fertilization and embryo transfer. Hum Reprod. 5:357-76).

Contrasting with the common use of GnRH agonists to inhibit LH and FSH secretion, the therapeutic use of their agonist property (to stimulate the LH and FSH secretion) has been very limited up to now.

In female infertility treatments, the ability of these substances to stimulate LH secretion has been used to trigger ovulation at mid-cycle (Lanzone, A et al., 1989 LH surge induction by GnRH agonist at the time of ovulation. Gynecol Endocrinol 3: 213-220; Buckett W. M. et al., 1998, Induction of the endogenous gonadotrophin surge for oocyte maturation with intra-nasal GnRH analogue (buserelin): effective minimal dose. Hum Reprod 13: 811-814, 1998; Fauser B C et al., 2002, Endocrine profile after triggering of final oocyte maturation with GnRH agonist after co-treatment with the GnRH antagonist Ganirelix during ovarian hyperstimulation for in vitro fertilisation. J Clin Endocrinol Metab 87: 709-715). However, in this case, the luteal phase was also found to be deficient and the pregnancy rate was low (Fauser B C et al., 2002, Endocrine profile after triggering of final oocyte maturation with GnRH agonist after co-treatment with the GnRH antagonist Ganirelix during ovarian hyperstimulation for in vitro fertilisation. J Clin Endocrinol Metab 87: 709-715; Beckers et al., 2003, Comparison of non-supplemented luteal phase characteristics following the administration of r-hCG, r-hLH or GnRH agonist to induce final oocyte maturation in in vitro fertilisation patients. J. Clin. Endocrinol. Metab. 88: 4186-4192).

Only one attempt to use GnRH agonist during the luteal phase has been reported in the medical literature (Schmidt-Sarosi C. et al., 1995, Ovulation triggering in clomiphene citrate-stimulated cycles: human chorionic gonadotropin versus a gonadotropin releasing hormone agonist. J Ass. Reprod. & Genetics. 12: 167-174). This attempt however failed as indicated in the report by the abnormaly low serum progesterone levels, a deficit in progesterone at the endometrium level, and low pregnancy rate.

It is noteworthy that a reduction in progesterone levels and luteal phase length has also been reported after only one or two administration of a GnRH agonist during the luteal phase of spontaneous cycles (Lemay et al., 1982, Sensitivity of pituitary and corpus luteum responses to single intranasal administration of buserelin in normal women. Fertil Steril 37: 193-200; Lemay et al., 1983, Gonadotroph and corpus luteum responses to two successive intranasal doses of a luteinising hormone-releasing hormone agonist at different days after the mid-cycle luteinising hormone surge, Fertil Steril 39: 661-667). In this second publication, Lemay et al. have shown that administration of a GnRH agonist impairs the luteal function and could lead to a new postcoidal contraceptive approach. All currently available evidences therefore point toward a negative effect of GnRH agonists on the luteal function and in any case no support effect. Therefore, up to date, GnRH agonists are considered by those skilled in the art and are essentially used as therapeutic agent to inhibit LH and FSH secretion through a desensitization mechanism, rather than to stimulate their secretion. This has been shown in international patent application WO95/16459 which discloses the administration to a female cattle of a LHRH analogue to desensitise the pituitary gland to endogenous LHRH activity.

Surprisingly, Applicant have shown that the use of a GnRH agonist in the preparation of a pharmaceutical agent for luteal support is fully possible and brings significant advantages when compared to agents currently used in this indication.

GnRH agonists can be used for luteal support either after a spontaneous ovulation, or after stimulation of follicular growth and induction of final follicular maturation and ovulation with one or several additional agents. In the latter case, the additional agent triggering final follicular maturation and ovulation can also be selected among GnRH agonists; another agonist or preferably the same agonist that the one used to support the luteal phase.

In some circumstances, a premature LH rise may occur during the follicle growth phase. This has a deleterious effect on the oocyte viability and can even trigger a premature ovulation, resulting in the treatment cycle cancellation. In order to prevent such premature LH rise, one can use the pharmaceutical agent suitable for luteal phase support after the administration of a GnRH antagonist which is administered during the last days of follicle growth stimulation (van Loenen A C et al., 2002; GnRH agonists, antagonists and assisted conception. Semin. Reprod. Med. 20: 349-364). The GnRH antagonist administration is typically initiated either on a fixed day of stimulation (e.g. 1 or 6) or as soon as follicles reached a mean diameter around 12 and 14 mm (Kolibianakis E M et al., 2003; Initiation of GnRH antagonist on day 1 as compared to day 6 of stimulation: effect on hormonal levels and follicular development in in vitro fertilization. J. Clin Endocrinol Metab, 88: 5632-5637). The GnRH antagonist can be cetrorelix, ganirelix or antide administered daily at a dose of 0.1 to 1 mg/day up to and including the day of ovulation trigger, or as a single administration of 1 to 10 mg. The GnRH antagonist can also be a nonpeptide antagonist such as TAK-013 (Takahito H. et al. 2003. Suppression of a Pituitary-Ovarian Axis by Chronic Oral Administration of a Novel Nonpeptide Gonadotropin-Releasing Hormone Antagonist, TAK-013, in Cynomolgus Monkeys J. Clin. Endocrinol. Metab. 2003 88: 1697-1704. Sasaki S, et al. 2003 Discovery of a thieno[2,3-d]pyrimidine-2,4-dione bearing a p-methoxyureidophenyl moiety at the 6-position: a highly potent and orally bioavailable non-peptide antagonist for the human luteinizing hormone-releasing hormone receptor. J Med Chem. 2003 Jan. 2; 46(1):113-24).

If most patients have an adequate luteal support when receiving a GnRH agonist according to the present invention, a minority may still have low serum progesterone levels, e.g. less than 10 ng/ml or a short luteal phase, e.g. less than 11 days. In this case, it is recommended to add to the GnRH agonist from the present invention, another luteal support such as natural progesterone, or a progestagen, or hCG, or LH, or one or more isoform of LH or of hCG, or a peptidomimetic of LH or of hCG, or an LH or an hCG analog with a modified pharmacokinetic, or a phosphodiesterase inhibitor, a non-peptidic modulator of cyclicAMP or a combination of two or more of these agents.

The combination of one or more of these pharmaceutical agents will however be done at lower doses than those used when the agent is used alone to support the luteal phase. According to a specific application of the present invention, follicular growth is stimulated with a folliculo-stimulating agent starting at the beginning of a spontaneous cycle or after induction of menstruation with a contraceptive pill or a progestagen. Agents stimulating follicular growth will be selected among hMG, urine-derived FSH, recombinant FSH, one or more FSH isoforms, FSH mimetics, FSH analogs with a modified pharmacokinetic (e.g. chimeric molecules), SERM, aromatase inhibitors, phosphodiesterase inhibitors, or a combination of two or more of these agents.

For example, SERM are selected among clomiphen(e), tamoxifen(e), or raloxifen(e) or a combination of two or more of these agents, while aromatase inhibitors can be selected among anastrozole, letrozole or exemestane or a combination of two or more of these agents.

Equally, according to the application of this invention, the use of a phosphodiesterase inhibitor such as theophylin, as agent stimulating follicular growth will allow to prolong the ovarian effect of endogenous and/or exogenous FSH by preventing the catabolism (i.e. the destruction) of FSH second messenger, namely cyclic AMP. This follicular stimulation can be followed by triggering final follicular maturation and ovulation with one or more of the following agents: hCG, or LH, or one or more isoform of LH or of hCG, or a peptidomimetic (nonpeptide analog) of LH or of hCG, or an LH or an hCG analog with a modified pharmacokinetic, or a phosphodiesterase inhibitor or a combination of two or more of these agents.

According to another application of the present invention, follicular growth stimulation and induction of ovulation is followed by an IUI or an oocyte recovery procedure. The oocytes will be used for in vitro maturation, in vitro fertilization for subsequent uterus transfer for an insemination.

All insemination methods are acceptable and the selection of one method is a medical decision. Sexual intercourses and IUI are usually recommended the day after triggering ovulation, and will eventually be repeated the day after. For IVF and ICSI, oocyte recovery must be done within a very precise timing, i.e. 34 to 40 hours after triggering final follicular maturation. For recovering the oocytes, the follicular fluid is aspirated using a needle guided with ultrasound. The aspirated fluid is examined under a binocular microscope for identifying cumulus-oocyte complexes. Those complexes are transferred in an appropriate culture medium and kept in an incubator maintaining well-defined and suitable temperature, humidity and gaz conditions.

According to the present invention, the luteal support provided by a GnRH agonist may be associated with a additional agent involved in the embryo implantation. Indeed, if an embryo implantation requires an endometrium prepared with an adequate luteal support, it is also known that other factors such as cytokines play a critical role in this process (Lessey B A. The role of the endometriun during embryo implantation. Hum Reprod 2000: 15 Suppl 6:39-50). A specific example is the critical role played by Leukemia Inhibitory Factor (LIF) in embryo implantation (Stewart CL et al. Blastocyst implantation depends on maternal expression of leukaemia inhibitory factor. Nature 1992; 359:76-9). In patients having implantation problems related to a relative or absolute LIF deficiency, it is recommended to add to the GnRH agonist for luteal support as described in the present invention, natural or native LIF, or recombinant LIF, or a peptide or a non-peptide agonist LIF analog and/or another cytokine involved in embryo implantation mechanisms.

The pharmaceutical agent containing the GnRH agonist used to support the luteal phase for infertility treatment of a female mammals, more specifically of woman, can be in a variety of well known formulations and administered using any of a variety of well known methods of administration such as intra-nasal, oral, sub-cutaneous, intra-muscular, vaginal, rectal, transdermal, pulmonary or the like, Non-injectable formulations are preferred and intra-nasally or inhaled formulations are particularly preferred.

In cases where the GnRH agonist is included in a suspension, the formulation may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, among others. Useful intra-nasal formulations of a GnRH agonist may contain a stabilizers and a surfactants. Among the pharmaceutically acceptable surfactants are polyoxyethylene castor oil derivatives, such as polyoxyethylene-glycerol-triricinoleate, also known as polyoxyl 35 caster oil (CREMOPHOR EL), or poloxyl 40 hydrogenated castor oil (CREMOPHOR RH40) both available from BASF Corp.; mono-fatty acid esters of polyoxyethylene (20) sorbitan, such as polyoxyethylene (20) sorbitan monolaurate (TWEEN 80), polyoxyethylene monostearate (TWEEN 60), polyoxyethylene (20) sorbitan monopalmitate (TWEEN 40), or polyoxyethylene 20 sorbitan monolaurate (TWEEN 20) (all available from ICI Surfactants of Wilmington, Del.); polyglyceryl esters, such as polyglyceryl oleate; and polyoxyethylated kernel oil (LABRAFL, available from Gattefosse Corp.). Preferably, the surfactant will be between about 0.01% and 10% by weight of the pharmaceutical composition. Among the pharmaceutically useful stabilizers are antioxidants such as sodium sulfite, sodium metabisulfite, sodium thiosulfate, sodium formaldehyde sulfoxylate, sulfur dioxide, ascorbic acid, isoascorbic acid, thioglycerol, thioglycolic acid, cysteine hydrochloride, acetyl cysteine, ascorbyl palmitate, hydroquinone, propyl gallate, nordihydroguaiaretic acid, butylated hydroxytoluene, butylated hydroxyanisole, alpha-tocopherol and lecithin. Preferably, the stabilizer will be between about 0.01% and 5% by weight of the pharmaceutical composition.

Suspensions may also include chelating agents such as ethylene diamine tetraacetic acid, its derivatives and salts thereof, dihydroxyethyl glycine, citric acid and tartaric acid among others. Additionally, proper fluidity of a suspension can be maintained, for example, by the use of coating materials such as lecithin, by the maintenance of the required particle size in the case of dispersions and by the use of surfactants, such as those previously mentioned.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or (a) fillers or extenders such as starches, lactose, sucrose, glucose, mannitol and silicic acid; (b) binders such as carboxymethylcellulose, alginates, gelatin, polyvinylpyrrolidone, sucrose and acacia; (c) humectants such as glycerol; (d) disintegrating agents such as agar-agar, calcium carbonate, potato or tapioca starch, alginic acid, certain silicates and sodium carbonate; (e) solution retarding agents such as paraffin; (f) absorption accelerators such as quaternary ammonium compounds; (g) wetting agents such as cetyl alcohol and glycerol monostearate; (h) absorbents such as kaolin and bentonite clay; and (i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, capsules, pills and granules can be prepared with coatings and shells such as enteric coating and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

This invention also envisages the use of GnRH agonists in a pharmaceutically acceptable salt form. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like. Certain basic compounds also form pharmaceutically acceptable salts, e.g., acid addition salts. For example, pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, pamoic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

The GnRH agonist used in the present invention may be selected among a native GnRH from mammals or any other animal species, or a recombinant, or a synthetic peptide agonist of GnRH, or a non-peptide agonist of GnRH, or a chimeric molecule of GnRH. The latter molecule may include a functional portion, peptide or non-peptide, of GnRH and will be obtained by molecular biology methods known by those skilled in the art. The GnRH agonist will preferrably have a high affinity for the GnRH receptor (e.g. $K_d$ between $10^{-13}$ M and $10^{-6}$ M; GnRH binding affinity test) (Loumaye E. et al. 1982; Binding affinity and biological activity of gonadotropin releasing hormone agonists in isolated pituitary cells. Endocrinology. 111:730-736). Moreover, its will be highly potent to stimulate LH release by the pituitary which can be documented in an in vitro bioassay using rat pituitary cells (e.g. $ED_{50}$ between $10^{-13}$ M and $10^{-6}$ M: GnRH Bioassay test) (Loumaye E et al., 1892. Binding affinity and biological activity of gonadotropin releasing hormone agonists in isolated pituitary cells. Endocrinology. 111:730-736).

GnRH agonists that can be used according to this invention, are well known and include, but are not limited to buserelin(e) ($<Glu^1-His^2-Trp^3-Ser^4-Tyr^5-D-Ser(t-But)^6-Leu^7-Arg^8-Pro^9-EA$ (SEQ ID NO: 2)), leuprorelin(e) ($<Glu^1-His^2-Trp^3-Ser^4-Tyr^5-D-Leu^6-Leu^7-Arg^8-Pro^9-EA$ (SEQ ID NO: 3)), triptorelin(e) ($<Glu^1-His^2-Trp^3-Ser^4-Tyr^5-D-Trp^6-Leu^7-Arg^8-Pro^9-Gly^{10}-NH_2$ (SEQ ID NO: 4)), goserelin(e) ($<Glu^1-His^2-Trp^3-Ser^4-Tyr^5-D-Ser(t-But)^6-Leu^7-Arg^8-Pro^9-AZA-Gly^1-NH_2$ (SEQ ID NO: 5)), and nafarelin ($<Glu^1-His^2-Trp^3-Ser^4-Tyr^5-D-Nal-(2)^6-Leu^7-Arg^8-Pro^9-Gly^{10}-NH_2$ (SEQ ID NO: 6)), deslorelin(e) and histrelin. Most of these agonists are commercially available whereas the others are known from the literature. Nonpeptide GnRH agonists can also be used such as compounds described, but not limited to, in WO0247722 which is incorporated herein as reference. More specifically, the GnRH agonist will be selected among a group of substances comprising buserelin(e), nafarelin(e), triptorelin(e), leuprorelin(e), goserelin(e), deslorelin(e) and histrelin(e) and analogs thereof with derived structures having essentially a GnRH activity, a combination of two or more of these agonists.

All these preferred GnRH agonists have in common to have a modified pharmacokinetic in comparison to native (natural) GnRH. This results in a higher biodisponiblity of these GnRH agonists because they remain available to pituitary receptors for a prolonged period after their administration.

The pharmaceutical agent containing the GnRH agonist used to support the luteal phase for infertility treatment will typically be administered within the first three days following ovulation trigger up to the moment a pregnancy is well established. Preferably, the administration will be started as soon as the first day following ovulation trigger. The dose of agonist is variable and will depend essentially of the agonist used, its pharmacokinetic and pharmacodynamic characteristics, as well as its mode of administration.

According to this invention, and preferably, the GnRH agonist used will be buserelin, the preferred route of administration will be intra-nasal, at one or several daily doses between 50 and 400 μg, preferably 100 μg.

The GnRH agonist administration frequency is also critical and must be defined for each agonist in regards of its pharmacokinetic and pharmacodynamic properties as well as its formulation. According to the preferred use, the pharmaceutically agent containing buserelin to be used for supporting the luteal phase during treatment of infertility, will be administered at a frequency between two times a day (on average at 12 hours interval) and one administration every three days, but preferentially one administration every day (approximately once every 24 hours).

The total period of administration of the GnRH agonist must cover at least the embryo pre-, peri- and early post-implantation period. After implantation, the embryo will indeed progressively secure its own luteal support through hCG secretion by trophoblast cells. Practically this means a duration of administration for the agonist between 7 and 28 days. Preferably, the total duration of buserelin administration will be 14 days.

The stimulation of follicular growth with FSH or derived compounds must last on average 10 days. The ovarian response to the stimulation is monitored by measuring, with ultrasound, the number and the diameter of all growing follicles. An additional method for this monitoring is to measure serum oestradiol levels (Shoham, 2001, Drug used for controlled ovarian stimulation: clomiphene citrate and gonadotropins. In *Textbook of Assisted Reproductive Techniques* eds D. K. Gardner, A. Weissman, C. M. Howles, Z. Shoham. Martin Dunitz 2001. pp 413-424; Balasch, 2001, Inducing follicular development in anovulatory patients and normally ovulating women: current concepts and the role of recombinant gonadotropins. In Textbook of Assisted Reproductive Techniques eds D. K. Gardner, A. Weissman, C. M. Howles, Z. Shoham. Martin Dunitz 2001 pp 425-446).

For agents stimulating endogenous FSH, such as SERM and aromatase inhibitors, they are usually administered by oral route for a period between one and seven days starting at the beginning of a menstrual cycle (Fisher et al. 2002, A randomized double-blind comparison of the effects of clomiphene citrate and the aromatase inhibitor letrozole on ovulatory function in normal women. Fertil Steril 78: 280-285).

A third possibility is to use phosphodiesterase inhibitors that will increase and prolong the ovarian effect of endogenous and/or exogenous FSH by preventing the catabolism (inactivation and destruction) of FSH second messenger i.e. cyclic AMP.

When a GnRH agonist is selected for triggering final follicular maturation, it will preferably, be the same that the agonist used to support the luteal phase. According to the present invention, it is preferred to use buserelin as GnRH agonist and the preferred mode of administration will be a single intra-nasal administration, at a dose between 50 and 600 μg, the preferred dose being 200 μg.

One variation of the present invention also forsees a pharmaceutical preparation suitable for delayed and controlled release of the agonist as defined in the present invention. The GnRH agonist can, for example, be incorporated in a matrix of biocompatible polymer allowing delayed and controlled release. All biocompatible polymers, well known by those skilled in the art are potential candidate to be used in this invention.

One additional aspect of the present invention is to provide a tool for treatment commonly called "kit", which will include one or several additional agents to trigger final follicular maturation, ovulation and the GnRH agonist to support the luteal phase. Preferably, the additional agent used to trigger final follicular maturation and ovulation will be the same as the agonist used to support the luteal phase. According to the present invention, the GnRH agonist is buserelin. Preferably, the additional agent used for triggering final follicular maturation and ovulation, as well as the agonist used for luteal support will be formulated in dosage and unit, or multiple units, sufficient for one to three, but preferably one cycle of treatment. The formulated product may be included in a packaging or an administration device easing the GnRH agonist administration to the patient.

Another aspect of the present invention is a method for treating infertility using GnRH agonists to support the luteal phase. This method includes use of a pharmaceutical agent such as a GnRH agonist to support the luteal phase as defined above in the description of the various ways to apply the invention.

This method can also include, before the luteal support phase, a phase consisting in the stimulation of follicle growth, final maturation of follicles, and ovulation with one or more additional agents, All the above-described embodiments may apply to this particular aspect of the present invention for treating infertility using GnRH agonists to support the luteal phase.

EXAMPLES

The present invention as well as the various ways to apply it, are illustrated by the following examples which are not limiting:

Example 1

Patients suffering from unexplained infertility, or from infertility resulting from mild to moderate endometrioisis, or an infertility resulting from a mild or moderate alteration of their partner sperm, and whom have not conceived despite regular sexual intercourses during a period of one or two years, usually undergo medical assistance. The most often used treatment is ovarian stimulation coupled to an IUI (Hughes G. H. 1997, The effectiveness of ovulation induction and intra-uterine insemination in the treatment of persistent infertility: a meta-analysis. Hum Reprod. 12: 1865-1872).

A prospective, randomised, parallel groups dose finding study was conducted in this patient population. After obtaining written informed consent, patient eligibility was confirmed and on day 1 to 5 of her next menstruation, the patient took orally for 5 days, 25 mg/day of exemestane, an aromatase inhibitor.

The ovarian response to treatment was followed on a regular basis using transvaginal ultrasound and by measuring serum oestradiol levels, Typically, a first assessment was performed on day 6 of the stimulation. The number and the size of each follicle was recorded. When at least one, and maximum three follicles reached a mean diameter of 16 mm or more, and that serum estradiol level does not indicate a significant risk of OHSS (i.e. serum estradiol <1500 pg/ml), the patient was randomely allocated to receive either one administration of GnRH agonist to trigger ovulation or one injection of hCG 5000 IU (control group). For that purpose the dose of buserelin administered intra-nasally, was 200 μg.

Between 12 and 48 hours after triggering ovulation, the patient's partner provided a sperm sample, after 2 to 5 days of abstinence. Motile sperm cells were separated from seminal fluid, dead sperm cells, leucocytes, and cellular debris using a suitable method such as a "swim-up" or a Percol gradient. On that same day, the motile sperm cell suspension was used to perform an intra-uterine insemination with a catheter inserted into the uterine cavity via the cervix. The procedure may be repeated on the next day.

From that day and for a period of 14 days, the patient received either no additional treatment (Patients in the hCG control group) or buserelin 100 μg every day IN, or every two days or every three days. These buserelin administrations were self-administered by the patient. These intra-nasal administrations took less than one minute, necessitated no preparation and no material, and did not carry the risk of adverse local reactions such as pain and abces. A pregnancy test was performed on day 14 of the luteal phase, and menstruation date was recorded for patient who did not conceived. The results presented below in tables 1-3 demonstrate a dose-depend luteal support by administration of a GnRH agonist during the luteal phase. Buserelin administered once a day provided a longer luteal phase, higher progesterone and oestradiol levels in late luteal phase and a trend toward a higher clinical pregnancy rate.

TABLE 1

Luteal phase duration (mean ± SD) and pregnancy test results in the four treatment groups.

| Treatment groups | hCG | Buserelin 100 μg/3 days | Buserelin 100 μg/2 days | Buserelin 100 μg/day |
|---|---|---|---|---|
| Patient (n) | 5 | 5 | 6 | 6 |
| Luteal phase duration (day) | 14.8 ± 1.1 | 14.8 ± 1.7 | 14.8 ± 3.3 | 15.3 ± 0.5 |
| Positive pregnancy test | 0/5 | 1/5 | 2/6 | 2/6 |
| Clinical pregnancy | 0/5 | 0/5 | 1/6 | 2/6 |

TABLE 2

Luteal phase serum progesterone levels in patients who did not conceive (ng/ml: mean ± SD).

| Treatment groups | Day 0 | Day 1 | Day 4 | Day 7 | Day 9 | Day 11 | Day 14 |
|---|---|---|---|---|---|---|---|
| hCG | 0.5 ± 0.3 | 1.1 ± 0.6 | 6.0 ± 4.7 | 12.3 ± 5.4 | 13.1 ± 3.5 | 9.7 ± 2.8 | 3.3 ± 1.7 |
| Buserelin 100 μg/3 days | 0.7 ± 0.3 | 0.9 ± 0.2 | 5.1 ± 2.0 | 11.5 ± 3.6 | 10.8 ± 6.6 | 10.0 ± 3.7 | 3.3 ± 2.4 |
| Buserelin 100 μg/2 days | 0.9 ± 0.7 | 1.3 ± 0.8 | 7.6 ± 3.2 | 11.7 ± 4.6 | 8.2 ± 6.4 | 8.3 ± 6.5 | 5.8 ± 4.7 |
| Buserelin 100 μg/day | 1.1 ± 0.4 | 1.2 ± 0.3 | 6.2 ± 2.3 | 13.9 ± 2.9 | 16.2 ± 7.5 | 14.1 ± 3.3 | 8.4 ± 4.3 |

TABLE 3

Luteal phase serum oestradiol levels in patients who did not conceive (pg/ml: mean ± SD).

| Treatment groups | Day 0 | Day 1 | Day 4 | Day 7 | Day 9 | Day 11 | Day 14 |
|---|---|---|---|---|---|---|---|
| hCG | 227 ± 74 | 189 ± 65 | 114 ± 35 | 166 ± 37 | 213 ± 41 | 190 ± 59 | 100 ± 52 |
| Buserelin 100 μg/3 days | 182 ± 76 | 325 ± 160 | 106 ± 61 | 144 ± 118 | 109 ± 88 | 123 ± 61 | 82 ± 31 |
| Buserelin 100 μg/2 days | 247 ± 79 | 164 ± 75 | 139 ± 77 | 70 ± 19 | 65 ± 15 | 75 ± 4 | 124 ± 68 |
| Buserelin 100 μg/day | 175 ± 071 | 213 ± 133 | 179 ± 101 | 163 ± 30 | 232 ± 77 | 200 ± 30 | 154 ± 85 |

Example 2

Patients from example 1 who were pregnant after 3 to 6 cycles of IUI, were proposed a treatment with IVF or ICSI. These treatments are proposed upfront to patients whom infertility cause is a severe tubal problem, or a severe endometriosis or a partner's severe sperm severe alteration. These patients can be treated prior her IVF or ICSI cycle with a oral contraceptive to precisely program their menstruation date.

This is done to better manage the couple and the ART center agenda. When menstruations occur, an ovarian stimulation was performed with FSH at a dose between 75 and 600 IU per day based on the patient's characteristics (e.g.: age, ovarian reserve status, weight, etc. . . . ). This treatment was done with FSH, but may also include clomiphene citrate or an aromatase inhibitor. Five to 7 days after the beginning of the stimulation, or when the leading follicles reached a mean diameter of 14 mm, a GnRH antagonist was administered to prevent a premature LH rise in the blood. Follicular growth was monitored using vaginal ultrasound and by measuring serum estradiol levels. These controls were performed every 2 to 3 days.

When at least two follicles reached a mean diameter of 16 mm or more, when the total number of follicles did not exceed 25 to 30, and when serum estradiol concentration did not indicate a risk for ovarian hyperstimulation (serum estradiol level <4000 pg/ml), the patient received one administration of GnRH agonist to trigger final follicular maturation. For that purpose, she received between 50 and 600 μg of busereline intra-nasaly, the preferred dose being 200 μg. The timing of buserelin administration was very precise since it defined the timing of oocyte retrieval procedure which must be done between 35 and 38 hours after the trigger.

On the second day after GnRH administration, the patient was admitted in the ART clinical unit for the oocyte retrieval procedure. Oocytes was retrieved by echoguided transvaginal aspiration of the follicles, This procedure was performed under light anesthesia. Aspirated follicular fluids were examined under binocular microscope to identify oocyte-cumulus complexes. These complexes were transferred in an appropriate culture medium, and maintain in an incubator in adequate temperature, gaz and humidity conditions. Several hours after retrieval, oocytes were inseminated either by co-incubation in a motile sperm cell suspension, or by direct injection of one sperm cell in the oocyte cytoplasm using a micro-manipulator. The patient left the ART center on that same day.

On the day preceeding the oocyte retrieval procedure, and for a period of 14 days, the patient received between 3 times a day and once every three days (preferably once a day), one intra-nasal administration of 50 to 400 μg of buserelin, preferably 100 μg. These intra-nasal administrations took less than one minute, did not necessitate any specific preparation and no material, and did not carry the risk of adverse local reactions such as pain and abces.

The day after insemination, fertilisation of the oocytes were assessed by visualizing under a microscope the presence of two pronuclei in the cytoplasm. The first cleavage stage of the embryos were observed within the next 48 hours. The embryo transfer into the uterus were usually be performed on day 3 after oocyte retrieval or later if the embryo culture was pursued up to the blastocyst stage. Most often, two embryos were replaced if the patient was less than 35 years old, and three were replaced if the patient was more than 35 years old. On day 13, after final follicular maturation trigger, a pregnancy test was performed by measuring hCG concentration in the patient's urines or blood (serum). A positive hCG test unquestionably means that the patient was pregnant since she did not receive exogenous hCG.

The invention claimed is:

1. A method of treating infertility in a female mammal comprising administering a pharmaceutical agent comprising a gonadotrophin releasing hormone (GnRH) agonist in an amount and for a time sufficient to support the luteal phase, wherein the GnRH agonist is administered to the female mammal beginning within the first three days after ovulation in the female mammal and for at least 7 days thereafter either
   i) after spontaneous ovulation in the female mammal, or
   ii) after stimulation of follicular growth and triggering of final follicular maturation followed by an ovulation in the female mammal by administration of at least one additional agent,
   such that infertility is treated in the female mammal.

2. The method according to claim 1, wherein the additional agent administered to trigger final follicular maturation and ovulation is a GnRH agonist different from the GnRH agonist administered to support the luteal phase.

3. The method according to claim 1, wherein the pharmaceutical agent which supports the luteal phase is administered after administration of a GnRH antagonist during the last days of follicular growth stimulation.

4. The method according to claim 1, wherein the pharmaceutical agent which supports the luteal phase is administered in combination with another luteal support agent selected from the group consisting of natural progesterone, a progestagen, human chorionic gonadotropin (hCG), luteinizing hormone (LH), one or more isoforms of LH or of hCG, a peptidomimetic of LH or of hCG, an LH or an hCG analog with a modified pharmacokinetic, a phosphodiesterase inhibitor, a non-peptidic modulator of cyclicAMP, and a combination of two or more of these agents.

5. The method according to claim 1, wherein the stimulation effected by the administration of the additional agent is followed, after ovulation trigger, with an intra-uterine insemination (IUI).

6. The method according to claim 1, wherein the GnRH agonist route of administration is selected from the group consisting of intra-nasal, oral, sub-cutaneous, intra-muscular, vaginal, rectal, transdermal, and pulmonary.

7. The method according to claim 1, wherein the additional agent triggering final follicular maturation and ovulation is selected from the group consisting of hCG, LH, one or more isoforms of hCG or LH, hCG and LH peptido-mimetics, hCG and LH analogs with a modified pharmacokinetic, phosphodiesterase inhibitors, and a combination of two or more of these agents.

8. The method according to claim 1, wherein the female mammal is a woman.

9. The method according to claim 1, wherein the administration of the GnRH agonist sufficient to support the luteal phase is for a duration of 7 to 14 days.

10. The method according to claim 1, wherein the administration of the GnRH agonist sufficient to support the luteal phase is for a duration of up to 28 days in a female mammal that has conceived.

11. The method according to claim 1, wherein the pharmaceutical agent which supports the luteal phase is administered in combination with a cytokine involved in embryo implantation mechanisms.

12. The method according to claim 11, wherein the cytokine is selected from the group consisting of native Leukemia Inhibitory Factor (LIF), recombinant LIF, a peptidic or a non-peptidic agonist analog of LIF, and a combination thereof.

13. The method according to claim 1, wherein the additional agent administered to trigger final follicular maturation and ovulation is a GnRH agonist which is the same as the GnRH agonist administered to support the luteal phase.

14. The method according to claim 13, wherein the GnRH agonist is buserelin and is administered intra-nasally, at least once, at a dose of between 50 and 600 µg.

15. The method according to claim 14, wherein buserelin is administered intra-nasally at a dose of 200 µg.

16. The method according to claim 1, wherein the GnRH agonist is selected from the group consisting of a natural (native) GnRH, a recombinant GnRH, a synthetic peptide agonist of GnRH, a non-peptide GnRH agonist, and a molecular chimera of GnRH.

17. The method according to claim 16, wherein the synthetic peptide is selected from the group comprising buserelin (e), nafarelin(e), triptorelin(e), leuprorelin(e), goserelin(e), deslorelin(e) and histrelin(e), analogs thereof, and a combination of two or more of these agonists.

18. The method according to claim 17, wherein the GnRH agonist is buserelin.

19. The method according to claim 1, wherein the stimulation effected by the administration of the additional agent is followed, before ovulation, by an oocyte retrieval procedure, wherein at least one oocyte is obtained.

20. The method according to claim 19, wherein the oocyte undergoes an in vitro maturation.

21. The method according to claim 19, wherein the oocyte undergoes an in vitro fertilization.

22. The method according to claim 1, wherein the additional agent stimulating follicular growth is selected from the group comprising human menopausal gonadotrophins (hMG), urine-derived follicle stimulating hormone (FSH), recombinant FSH, one or several FSH isoforms, FSH mimetics, FSH analogs with a modified phamacokinetic, selective estrogen receptors modulators (SERM), aromatases inhibitors, phosphodiesterase inhibitors, and a combination of two or more of these agents.

23. The method according to claim 22, wherein the SERM is selected from the group consisting of clomiphen(e), tamoxifen(e), raloxifen(e), and a combination of two or more of these agents.

24. The method according to claim 22, wherein the aromatase inhibitor is selected from the group consisting of anastrozole, letrozole, exemestane, and a combination of two or more of these agents.

25. The method according to claim 22, wherein the phosphodiesterase inhibitor is theophyline.

26. A method of treating infertility in a female mammal comprising administering a pharmaceutical agent which comprises a GnRH agonist comprising buserelin, which supports luteal phase after stimulation of follicular growth and induction of final follicular maturation and ovulation with one or more additional agents, wherein said buserelin is administered intra-nasally within the first three days following ovulation trigger at a dose of between 50 and 400 μg and at a frequency between three times a day and once every three days for a duration of 7 to 14 days, such that infertility in the female mammal is treated.

27. The method according to claim 26, wherein buserelin is administered on the first day following ovulation trigger.

28. The method according to claim 26, wherein buserelin is administered at a dose of 100 μg.

29. The method according to claim 26, wherein buserelin is administered for a duration of 14 days.

30. A method of treating infertility in a female mammal comprising administering a pharmaceutical agent which comprises a GnRH agonist comprising buserelin, which supports luteal phase after stimulation of follicular growth and induction of final follicular maturation and ovulation with one or more additional agents, wherein said buserelin is administered intra-nasally within the first three days following ovulation trigger at a dose of between 50 and 400 μg and at a frequency between three times a day and once every three days for a duration of up to 28 days in a female mammal that has conceived, such that infertility in the female mammal is treated.

* * * * *

UNITED STATES PATENT AND TRADEMARK OFFICE
CERTIFICATE OF CORRECTION

PATENT NO. : 7,671,027 B2  Page 1 of 1
APPLICATION NO. : 10/540228
DATED : March 2, 2010
INVENTOR(S) : Ernest Loumaye It is certified that error appears in the above-identified patent and that said Letters Patent is hereby corrected as shown below:

On page 9, column 15, line 17, please change "who were pregnant" to --who were not pregnant--.

Signed and Sealed this

Third Day of August, 2010

David J. Kappos
*Director of the United States Patent and Trademark Office*